(12) United States Patent
Hartwell

(10) Patent No.: US 9,987,402 B2
(45) Date of Patent: *Jun. 5, 2018

(54) APPARATUS AND METHOD FOR WOUND VOLUME MEASUREMENT

(71) Applicant: Smith & Nephew PLC, London (GB)

(72) Inventor: Edward Hartwell, York (GB)

(73) Assignee: Smith & Nephew PLC, London (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/946,468

(22) Filed: Nov. 19, 2015

(65) Prior Publication Data

US 2016/0166740 A1    Jun. 16, 2016

Related U.S. Application Data

(60) Continuation of application No. 14/455,200, filed on Aug. 8, 2014, now Pat. No. 9,192,332, which is a (Continued)

(30) Foreign Application Priority Data

Dec. 6, 2007    (GB) .................................. 0723855.3

(51) Int. Cl.
*A61M 5/00* (2006.01)
*A61M 1/00* (2006.01)
(Continued)

(52) U.S. Cl.
CPC .......... *A61M 1/0025* (2014.02); *A61B 5/0055* (2013.01); *A61B 5/107* (2013.01);
(Continued)

(58) Field of Classification Search
CPC .......... A61M 5/00; A61M 3/00; A61M 25/00; A61M 35/00; A61M 1/00; A61M 5/178; A61F 13/00; A61F 7/00
See application file for complete search history.

(56) References Cited

U.S. PATENT DOCUMENTS

| 3,972,328 A | 8/1976 | Chen |
| 4,062,012 A | 12/1977 | Colbert et al. |

(Continued)

FOREIGN PATENT DOCUMENTS

| CN | 101385887 A | 3/2009 |
| CN | 101616700 | 12/2009 |

(Continued)

OTHER PUBLICATIONS

U.S. Appl. No. 61/828,604, filed May 29, 2013, Collinson et al.
(Continued)

*Primary Examiner* — Tatyana Zalukaeva
*Assistant Examiner* — Ilya Treyger
(74) *Attorney, Agent, or Firm* — Knobbe, Martens, Olson & Bear LLP

(57) ABSTRACT

A method and apparatus for measuring a volume of a wound are described, the method comprising the steps of: applying a dressing over a wound, the volume of which is to be measured, the dressing including at least a sealing drape over the wound so as to create a sealed wound cavity; creating a vacuum in said wound cavity by vacuum pump means so as to produce a predetermined vacuum in the wound cavity; measuring a volume of air extracted from said wound cavity in producing said predetermined vacuum; and, calculating a volume of said wound.

20 Claims, 9 Drawing Sheets

Related U.S. Application Data division of application No. 12/746,492, filed as application No. PCT/GB2008/050917 on Oct. 7, 2008, now Pat. No. 8,814,841.

(51) Int. Cl.

| | | |
|---|---|---|
| *A61B 5/107* | (2006.01) | |
| *A61B 5/00* | (2006.01) | |
| *A61F 13/00* | (2006.01) | |
| *A61M 25/00* | (2006.01) | |
| *A61M 35/00* | (2006.01) | |

(52) U.S. Cl.
CPC ............ *A61B 5/1073* (2013.01); *A61B 5/445* (2013.01); *A61B 5/7278* (2013.01); *A61B 5/742* (2013.01); *A61F 13/00* (2013.01); *A61M 1/0088* (2013.01); *A61B 5/6843* (2013.01); *A61M 2205/15* (2013.01); *A61M 2205/18* (2013.01); *A61M 2205/3331* (2013.01); *A61M 2205/3344* (2013.01); *A61M 2205/50* (2013.01); *A61M 2230/00* (2013.01)

(56) References Cited

U.S. PATENT DOCUMENTS

| | | |
|---|---|---|
| 4,643,641 A | 2/1987 | Clausen et al. |
| 4,969,880 A | 11/1990 | Zamierowski |
| 5,127,388 A | 7/1992 | Cicalese et al. |
| 5,238,732 A | 8/1993 | Krishnan |
| 5,358,494 A | 10/1994 | Svedman |
| 5,417,743 A | 5/1995 | Dauber |
| 5,437,651 A | 8/1995 | Todd et al. |
| 5,449,347 A | 9/1995 | Preen et al. |
| 5,449,584 A | 9/1995 | Banba et al. |
| 5,549,584 A | 8/1996 | Gross |
| 5,616,121 A | 4/1997 | McKay |
| 5,676,525 A | 10/1997 | Berner et al. |
| 5,759,570 A | 6/1998 | Arnold |
| 5,827,246 A | 10/1998 | Bowen |
| 6,071,267 A | 6/2000 | Zamierowski |
| 6,162,194 A | 12/2000 | Shipp |
| 6,193,658 B1 | 2/2001 | Wendelken et al. |
| 6,626,891 B2 | 9/2003 | Ohmstede |
| 6,673,036 B1 | 1/2004 | Britto |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,756,903 B2 | 6/2004 | Omry et al. |
| 6,936,037 B2 | 8/2005 | Bubb |
| 6,951,553 B2 | 10/2005 | Bubb et al. |
| 6,979,324 B2 | 12/2005 | Bybordi et al. |
| 7,022,113 B2 | 4/2006 | Lockwood et al. |
| 7,041,057 B1 | 5/2006 | Faupel et al. |
| 7,108,683 B2 | 9/2006 | Zamierowski |
| 7,361,184 B2 | 4/2008 | Joshi |
| 7,381,859 B2 | 6/2008 | Hunt et al. |
| 7,524,315 B2 | 4/2009 | Blott et al. |
| 7,569,742 B2 | 8/2009 | Haggstrom et al. |
| 7,615,036 B2 | 11/2009 | Joshi et al. |
| 7,625,362 B2 | 12/2009 | Boehringer et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,909,805 B2 | 3/2011 | Weston |
| 7,910,791 B2 | 3/2011 | Coffey |
| 7,922,703 B2 | 4/2011 | Riesinger |
| 7,927,319 B2 | 4/2011 | Lawhorn |
| 7,964,766 B2 | 6/2011 | Blott et al. |
| 8,025,052 B2 | 9/2011 | Matthews et al. |
| 8,062,272 B2 | 11/2011 | Weston |
| 8,062,331 B2 | 11/2011 | Zamierowski |
| 8,080,702 B2 | 12/2011 | Blott et al. |
| 8,105,295 B2 | 1/2012 | Blott et al. |
| 8,118,794 B2 | 2/2012 | Weston et al. |
| 8,152,785 B2 | 4/2012 | Vitaris |
| 8,162,907 B2 | 4/2012 | Heagle |
| 8,207,392 B2 | 6/2012 | Haggstrom et al. |
| 8,241,018 B2 | 8/2012 | Harr |
| 8,241,261 B2 | 8/2012 | Randolph et al. |
| 8,282,611 B2 | 10/2012 | Weston |
| 8,294,586 B2 | 10/2012 | Pidgeon et al. |
| 8,303,552 B2 | 11/2012 | Weston |
| 8,308,714 B2 | 11/2012 | Weston et al. |
| 8,317,774 B2 | 11/2012 | Adahan |
| 8,323,264 B2 | 12/2012 | Weston et al. |
| 8,372,049 B2 | 2/2013 | Jaeb et al. |
| 8,372,050 B2 | 2/2013 | Jaeb et al. |
| 8,398,614 B2 | 3/2013 | Blott et al. |
| D679,819 S | 4/2013 | Peron |
| D679,820 S | 4/2013 | Peron |
| 8,425,478 B2 | 4/2013 | Olson |
| 8,444,612 B2 | 5/2013 | Patel et al. |
| 8,449,509 B2 | 5/2013 | Weston |
| 8,460,255 B2 | 6/2013 | Joshi et al. |
| 8,628,505 B2 | 1/2014 | Weston |
| 8,641,691 B2 | 2/2014 | Fink |
| 8,663,198 B2 | 3/2014 | Buan et al. |
| 8,663,200 B2 | 3/2014 | Weston et al. |
| 8,715,256 B2 | 5/2014 | Greener |
| 8,734,425 B2 | 5/2014 | Nicolini |
| 8,764,732 B2 | 7/2014 | Hartwell |
| 8,795,243 B2 | 8/2014 | Weston |
| 8,808,274 B2 | 8/2014 | Hartwell |
| 8,814,841 B2 | 8/2014 | Hartwell |
| 8,829,263 B2 | 9/2014 | Haggstrom et al. |
| 8,834,451 B2 | 9/2014 | Blott et al. |
| 8,843,327 B2 | 9/2014 | Vernon-Harcourt et al. |
| 8,845,603 B2 | 9/2014 | Middleton et al. |
| 8,905,985 B2 | 12/2014 | Allen |
| 8,945,074 B2 | 2/2015 | Buan et al. |
| 8,951,235 B2 | 2/2015 | Allen et al. |
| 8,956,336 B2 | 2/2015 | Haggstrom et al. |
| 9,061,095 B2 | 6/2015 | Adie et al. |
| 9,067,003 B2 | 6/2015 | Buan et al. |
| 9,084,845 B2 | 7/2015 | Adie et al. |
| 9,192,332 B2 | 11/2015 | Hartwell |
| 9,199,012 B2 | 12/2015 | Vitaris et al. |
| 9,220,822 B2 | 12/2015 | Hartwell et al. |
| 9,220,823 B2 | 12/2015 | Nicolini et al. |
| 2002/0026946 A1 | 3/2002 | McKay |
| 2002/0198504 A1 | 12/2002 | Risk et al. |
| 2003/0040687 A1 | 2/2003 | Boynton et al. |
| 2004/0118460 A1 | 6/2004 | Stinson |
| 2005/0251117 A1 | 11/2005 | Anderson et al. |
| 2005/0267402 A1 | 12/2005 | Stewart et al. |
| 2005/0272142 A1 | 12/2005 | Horita |
| 2006/0009744 A1 | 1/2006 | Erdman et al. |
| 2006/0019144 A1 | 1/2006 | Hidaka et al. |
| 2006/0083623 A1 | 4/2006 | Higgins et al. |
| 2006/0122558 A1 | 6/2006 | Sherman et al. |
| 2006/0192259 A1 | 8/2006 | Silverbrook |
| 2006/0282174 A1 | 12/2006 | Haines |
| 2006/0282175 A1 | 12/2006 | Haines et al. |
| 2006/0287632 A1 | 12/2006 | Sarangapani |
| 2007/0016152 A1 | 1/2007 | Karpowicz et al. |
| 2007/0032762 A1 | 2/2007 | Vogel |
| 2007/0055209 A1 | 3/2007 | Patel et al. |
| 2007/0091614 A1 | 4/2007 | Kaisser et al. |
| 2007/0219532 A1 | 9/2007 | Karpowicz et al. |
| 2007/0225663 A1 | 9/2007 | Watt et al. |
| 2007/0260226 A1 | 11/2007 | Jaeb et al. |
| 2007/0276195 A1 | 11/2007 | Xu et al. |
| 2007/0276309 A1 | 11/2007 | Xu et al. |
| 2008/0071161 A1 | 3/2008 | Jaeb et al. |
| 2008/0071216 A1 | 3/2008 | Locke et al. |

(56) References Cited

U.S. PATENT DOCUMENTS

| | | |
|---|---|---|
| 2008/0281281 A1 | 11/2008 | Meyer et al. |
| 2008/0306456 A1 | 12/2008 | Riesinger |
| 2009/0012441 A1 | 1/2009 | Mulligan |
| 2009/0030402 A1 | 1/2009 | Adahan |
| 2009/0114293 A1 | 5/2009 | Kanai et al. |
| 2009/0116712 A1 | 5/2009 | Al-Moosawi et al. |
| 2009/0123513 A1 | 5/2009 | Greener |
| 2009/0125004 A1 | 5/2009 | Shen et al. |
| 2009/0129986 A1 | 5/2009 | Wimberger-Friedl et al. |
| 2009/0149821 A1 | 6/2009 | Scherson et al. |
| 2009/0166411 A1 | 7/2009 | Kramer et al. |
| 2009/0227969 A1 | 9/2009 | Jaeb et al. |
| 2009/0234306 A1 | 9/2009 | Vitaris |
| 2009/0270833 A1 | 10/2009 | DeBelser et al. |
| 2009/0292264 A1 | 11/2009 | Hudspeth et al. |
| 2009/0299251 A1 | 12/2009 | Buan |
| 2009/0299306 A1 | 12/2009 | Buan |
| 2010/0036367 A1 | 2/2010 | Krohn |
| 2010/0042059 A1 | 2/2010 | Pratt et al. |
| 2010/0068820 A1 | 3/2010 | Meathrel et al. |
| 2010/0125258 A1 | 5/2010 | Coulthard et al. |
| 2010/0126484 A1 | 5/2010 | Skell et al. |
| 2010/0191126 A1 | 7/2010 | Al-Moosawi et al. |
| 2010/0211030 A1 | 8/2010 | Turner et al. |
| 2010/0244780 A1 | 9/2010 | Turner |
| 2010/0249733 A9 | 9/2010 | Blott |
| 2010/0265649 A1 | 10/2010 | Singh et al. |
| 2010/0305526 A1 | 12/2010 | Robinson et al. |
| 2010/0324510 A1 | 12/2010 | Andresen et al. |
| 2011/0004172 A1 | 1/2011 | Eckstein et al. |
| 2011/0054423 A1 | 3/2011 | Blott et al. |
| 2011/0077605 A1 | 3/2011 | Karpowicz et al. |
| 2011/0098600 A1 | 4/2011 | Matsumura et al. |
| 2011/0118683 A1 | 5/2011 | Weston |
| 2011/0202220 A1 | 8/2011 | Seta et al. |
| 2011/0224631 A1 | 9/2011 | Simmons |
| 2011/0236265 A1 | 9/2011 | Hasui et al. |
| 2011/0236277 A1 | 9/2011 | Lee et al. |
| 2011/0257572 A1 | 10/2011 | Locke et al. |
| 2012/0035469 A1 | 2/2012 | Whelan et al. |
| 2012/0041399 A1 | 2/2012 | Blott et al. |
| 2012/0259299 A1 | 10/2012 | Ryu et al. |
| 2012/0271256 A1 | 10/2012 | Locke et al. |
| 2013/0085462 A1 | 4/2013 | Nip et al. |
| 2013/0116635 A1 | 5/2013 | Fleischmann |
| 2013/0138054 A1 | 5/2013 | Fleischmann |
| 2013/0144230 A1 | 6/2013 | Wu et al. |
| 2013/0150813 A1 | 6/2013 | Gordon |
| 2013/0150814 A1 | 6/2013 | Buan |
| 2013/0165878 A1 | 6/2013 | Heagle |
| 2013/0267917 A1 | 10/2013 | Pan et al. |
| 2013/0274688 A1 | 10/2013 | Weston |
| 2013/0331822 A1 | 12/2013 | Patel et al. |
| 2014/0114268 A1 | 4/2014 | Auguste et al. |
| 2014/0163490 A1 | 6/2014 | Locke et al. |
| 2014/0163493 A1 | 6/2014 | Weston et al. |
| 2014/0228791 A1 | 8/2014 | Hartwell |
| 2014/0276487 A1 | 9/2014 | Locke et al. |
| 2014/0316359 A1 | 10/2014 | Collinson et al. |
| 2015/0025482 A1 | 1/2015 | Begin et al. |
| 2015/0032035 A1 | 1/2015 | Banwell et al. |
| 2015/0051560 A1 | 2/2015 | Askem |
| 2015/0174304 A1 | 6/2015 | Askem et al. |
| 2015/0217032 A1 | 8/2015 | Allen et al. |
| 2016/0166741 A1 | 6/2016 | Nicolini |

FOREIGN PATENT DOCUMENTS

| | | | |
|---|---|---|---|
| CN | 103221077 | | 7/2013 |
| EP | 0 208 395 | | 1/1987 |
| EP | 1 476 217 | | 11/2004 |
| EP | 2 302 127 A1 | | 3/2011 |
| EP | 2 462 908 | | 6/2012 |
| EP | 2 544 642 | | 1/2015 |
| EP | 2 648 668 | | 1/2015 |
| EP | 2 836 711 | | 2/2015 |
| FR | 1163907 | | 10/1958 |
| GB | 2342584 | | 4/2000 |
| JP | 2000-105011 | | 4/2000 |
| JP | 2001-241382 | | 9/2001 |
| JP | 2001-286807 | | 10/2001 |
| JP | 2010-185458 | | 5/2010 |
| WO | WO 1994/20041 | | 9/1994 |
| WO | WO 1994/21312 | | 9/1994 |
| WO | WO 1996/05873 | | 2/1996 |
| WO | WO 1998/19068 | | 5/1998 |
| WO | WO 2000/07653 | | 2/2000 |
| WO | WO 2000/21586 | | 4/2000 |
| WO | WO 2000/49968 | | 8/2000 |
| WO | WO 2000/56378 | | 9/2000 |
| WO | WO 2000/61206 | | 10/2000 |
| WO | WO 03/005943 | * | 7/2001 |
| WO | WO 2003/005943 | | 1/2003 |
| WO | WO 2003/057307 | | 7/2003 |
| WO | WO 2004/037334 | | 5/2004 |
| WO | WO 2005/046760 | | 5/2005 |
| WO | WO 2005/046761 | | 5/2005 |
| WO | WO 2005/046762 | | 5/2005 |
| WO | WO 2006/052745 | * | 9/2005 |
| WO | WO 2005/105180 | | 11/2005 |
| WO | WO 2005/123170 | | 12/2005 |
| WO | WO 2006/046060 | | 5/2006 |
| WO | WO 2006/052745 | | 5/2006 |
| WO | WO 2006/052839 | | 5/2006 |
| WO | WO 2006/117207 | | 11/2006 |
| WO | WO 2007/019038 | | 2/2007 |
| WO | WO 2007/087811 | | 8/2007 |
| WO | WO 2008/036345 | | 3/2008 |
| WO | WO 2008/039223 | | 4/2008 |
| WO | WO 2008/048481 | | 4/2008 |
| WO | WO 2008/049029 | | 4/2008 |
| WO | WO 2008/100440 | | 8/2008 |
| WO | WO 2008/135997 | | 11/2008 |
| WO | WO 2008/154158 | | 12/2008 |
| WO | WO 2009/019415 | | 2/2009 |
| WO | WO 2009/047524 | | 4/2009 |
| WO | WO 2009/066104 | | 5/2009 |
| WO | WO 2009/071924 | | 6/2009 |
| WO | WO 2009/089390 | | 7/2009 |
| WO | WO 2009/103031 | | 8/2009 |
| WO | WO 2009/124100 | | 10/2009 |
| WO | WO 2009/158128 | | 12/2009 |
| WO | WO 2010/017484 | | 2/2010 |
| WO | WO 2010/021783 | | 2/2010 |
| WO | WO 2010/039481 | | 4/2010 |
| WO | WO 2010/051418 | | 5/2010 |
| WO | WO 2010/072349 | | 7/2010 |
| WO | WO 2010/093753 | | 8/2010 |
| WO | WO 2010/126444 | | 11/2010 |
| WO | WO 2010/142959 | | 12/2010 |
| WO | WO 2010/147533 | | 12/2010 |
| WO | WO 2011/087871 | | 10/2011 |
| WO | WO 2011/135285 | | 11/2011 |
| WO | WO 2011/135286 | | 11/2011 |
| WO | WO 2011/135287 | | 11/2011 |
| WO | WO 2011/144888 | | 11/2011 |
| WO | WO 2012/131237 | | 10/2012 |
| WO | WO 2012/140378 | | 10/2012 |
| WO | WO 2012/143665 | | 10/2012 |
| WO | WO 2013/010907 | | 1/2013 |
| WO | WO 2012/038724 | | 3/2013 |
| WO | WO 2013/064852 | | 5/2013 |
| WO | WO 2013/083800 | | 6/2013 |
| WO | WO 2013/118447 | | 8/2013 |
| WO | WO 2013/140255 | | 9/2013 |
| WO | WO 2013/149078 | | 10/2013 |
| WO | WO 2014/008348 | | 1/2014 |
| WO | WO 2014/016759 | | 1/2014 |
| WO | WO 2014/020440 | | 2/2014 |
| WO | WO 2014/020443 | | 2/2014 |
| WO | WO 2014/108476 | | 7/2014 |
| WO | WO 2014/113253 | | 7/2014 |

(56) References Cited

FOREIGN PATENT DOCUMENTS

| WO | WO 2015/022334 | 2/2015 |
|---|---|---|
| WO | WO 2015/022340 | 2/2015 |

OTHER PUBLICATIONS

U.S. Appl. No. 61/829,187, filed May 30, 2013, Collinson et al.
U.S. Appl. No. 61/906,865, filed Nov. 20, 2013, Collinson et al.
U.S. Appl. No. 61/907,350, filed Nov. 21, 2013, Collinson et al.
ActiV.A.C. Therapy System User Manual, KCI, dated Sep. 2007, in 64 pages.
International Preliminary Report on Patentability re PCT Application No. PCT/US2011/059016 dated Apr. 29, 2014.
International Preliminary Report on Patentability dated Mar. 26, 2013 in International Application No. PCT/GB2011/051745 in 7 pages.
International Search Report and Written Opinion re PCT Application No. PCT/US2011/059016 dated Apr. 23, 2014.
International Search Report and Written Opinion re PCT/IB2011/002943, dated Jan. 28, 2013.
International Search Report for PCT Application No. PCT/GB2011/051745, dated Feb. 2, 2012.
Invitation to Pay Additional Fees for International Application No. PCT/US2011/059016 dated Feb. 17, 2014 in 7 pages.
Notice of Opposition to EPO Patent No. EP 2 618 860, dated Mar. 16, 2016, in 5 pages.
Office Action dated Aug. 15, 2013 in U.S. Appl. No. 13/824,982 in 14 pages.
Opposition—Statement of Facts and Evidence for Opposition to EPO Patent No. EP 2 618 860, filed Mar. 16, 2016, in 9 pages.
U.S. Appl. No. 14/972,734, filed Dec. 17, 2015, Nicolni.
International Preliminary Report on Patentability for PCT/GB2008/050917, dated Jun. 8, 2010. in 7 pages.
International Search Report for PCT/GB2008/050917, dated Jan. 14, 2009. in 5 pages.
The American Heritage Dictionary of the English Language, Fourth Edition, 2000.
Kendall ULTEC Hydrocolloid Dressing (4"×4"), product ordering page, web page downloaded Jul. 13, 2014.
Protz, Kerstin: "Modern Wundauflagen unterstutzen Heilungsprozess", Wundversorgung: Indikation and Anwendung, Geriatrie Journal, Apr. 2005, pp. 3333-3339, with translation.
U.S. Appl. No. 13/824,982, U.S. Pat. No. 8,734,425.
U.S. Appl. No. 12/746,492, U.S. Pat. No. 8,814,841.
U.S. Appl. No. 14/455,200, U.S. Pat. No. 9,192,332.
U.S. Appl. No. 14/256,658, U.S. Pat. No. 9,220,823.
U.S. Appl. No. 14/972,734.
U.S. Appl. No. 13/287,959, U.S. Pat. No. 8,905,985.
U.S. Appl. No. 13/403,715, U.S. Pat. No. 8,951,235.
U.S. Appl. No. 14/598,083, 2015/0217032.
U.S. Appl. No. 12/455,043, U.S. Pat. No. 8,308,714.
U.S. Appl. No. 13/665,397, U.S. Pat. No. 8,663,200.
U.S. Appl. No. 14/179,434, 2014/0163493.
U.S. Appl. No. 14/972,734, 2006/0166741.
U.S. Appl. No. 12/445,043, U.S. Pat. No. 8,308,714.
Diels, K. et al., "Leybold Vacuum Handbook", translated by Adam, H. et al, Pergamon Press, 1966, in 10 pages.
Martin, L.H. et al., "A Manual of Vacuum Practice", Melbourne University Press, first published 1947, reprinted 1948, in 12 pages.
Brief Communication—Letter from the Proprietor, re the Opposition of European Patent No. EP 2 237 724, dated Jun. 19, 2017, in 24 pages.
Notice of Opposition—Statement of Facts and Evidence, re European Patent No. EP 2 237 724, dated Dec. 30, 2016, in 15 pages.
Reply of the Patent Proprietor to the Notice(s) of Opposition, re the Oppostion of European Patent No. EP 2 237 724, dated May 31, 2017, in 9 pages.

\* cited by examiner

APPARATUS AND METHOD FOR WOUND VOLUME MEASUREMENT

The present invention relates to apparatus and a method for the measurement of wound volume to assess progress of wound healing particularly, though not exclusively, during topical negative pressure (TNP) therapy.

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

One particular area of wound therapy which is desirable is to monitor the volume of a wound during its treatment such as, for example, at dressing change time so as to be able to quantify the healing process. However, there are presently no simple and/or accurate tools with which to make this assessment of wound volume.

Methods which have been used have include measuring the length, width and depth of a wound and making some assessment from the dimensions but this is very inaccurate; Taking a tracing around the wound, calculating the area and taking depth measurements; filling the wound with a filler and measuring the wound volume based on a known density of the filler; and photographic methods. All of these prior methods involve making calculated guesses resulting in inaccurate volume figures or are time consuming or are rather impractical.

Desirably, wound volume should be measured when a dressing is changed at, for example, every few days so as to keep a continuous record of progress.

Whatever method was used it would result in the figures having to be stored in a file, for example, and generally not with the patient being treated.

It is an aim of the present invention to at least partly mitigate the above-mentioned problems.

According to a first aspect of the present invention there is provided a method of measuring a volume of a wound, the method comprising the steps of: applying a dressing over a wound, the volume of which is to be measured, the dressing including at least a sealing drape over the wound so as to create a sealed wound cavity; creating a vacuum in said wound cavity by vacuum pump means so as to produce a predetermined vacuum in the wound cavity; measuring a volume of air extracted from said wound cavity in producing said predetermined vacuum; and, calculating a volume of said wound.

According to a second aspect of the present invention there is provided apparatus for measuring the volume of a wound, the apparatus comprising: a dressing covering and sealing the wound to form a cavity over the wound; an aspiration conduit leading from the wound cavity to a waste canister; a vacuum source; and, flow measuring sensor means.

In one embodiment of the present invention, the volume of air may be measured by signals received from flow sensor means in an apparatus control system.

Desirably, the wound volume measurement may be made at a time of dressing change and with an empty waste canister.

Desirably, the wound may be dressed in the same manner as closely as possible each time so as to minimise variables due to differences in the type and degree of packing of the wound, for example. For example, the wound may be packed with suitable filler material (if large enough and if appropriate) such as gauze, foam or any other type of filler appropriate to the wound and the sealing drape may be applied such that when the filler is compressed by the applied vacuum to the predetermined vacuum pressure then the sealing drape may be flush, for example, with the patient's sound flesh surrounding the wound. This is explanation is merely exemplary but is intended to emphasize the desirability of a consistent manner of wound dressing.

The method of the present may be applied by apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

When the dressing is applied to the wound a volume of air is trapped under the sealing drape in the wound cavity. When the vacuum source such as a vacuum pump, for example, is started the wound cavity is evacuated to a predetermined vacuum such as by 0.1 of an atmosphere (i.e. about 76 mmHg below atmospheric pressure). In this case 0.1 of the volume of air in the wound cavity is removed and which is measured by the flow sensor means such as a flowmeter, for example, in the control and monitoring system. The volume of air removed will be proportional to the actual volume of the wound. The volumes of other parts of the apparatus such as the aspiration conduit, the waste canister, the vacuum pump and the flow conduits in the apparatus leading to the flow sensor may be measured and/or are known and constant factors for which a correction factor may be incorporated in memory means in the control system software.

Once the desired vacuum level is achieved and is steady at that level, the various factors may be computed by the software in the control system to calculate the wound volume. It is important that the desired vacuum is at a steady state and the vacuum source such as a vacuum pump may be running slowly or intermittently to achieve such a steady state due, for example, to a leak into the wound cavity through or around the sealing drape. The software may contain appropriate data relating to the vacuum pump operating regime to calculate the steady state leak rate and to enable the control and monitoring system to apply a suitable correction factor to allow for a steady state leak rate. Thus, when the wound cavity has achieved a steady state when the vacuum level pressure is at the desired value, what the flow sensor is reading is the actual leak rate which may be used by the software to compute the correction factor applicable.

Different wound filling materials may have different compressibility from each other. Gauze, for example, is made from material fibres which themselves are virtually incompressible at the levels of vacuum under consideration in the present invention; foam materials, however, are much more compressible and thus, correction factors need to be made to allow for the type of wound filling material in use. This may be easily achieved by test cavities of known volumes used to calibrate the apparatus for different filling materials and calculate appropriate correction factors.

As noted above it is desirable that at a time of dressing change the waste canister is empty since its empty volume forms part of the correction factor incorporated into the software. However, it is not necessary that the waste canister be empty so long as its free space is known so that a suitable factor may be entered into the control and monitoring system such as by a key pad associated with the apparatus device, for example.

In the present invention the device may have means such as LED display means, for example, of displaying and storing the volume of the wound as measured at each stage such as at each dressing change time, for example, so that a record exists of the progress of wound healing. Alternatively, the device may have an output to a separate display and/or recording device where data may be held and/or displayed.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable alarm means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus.

In order that the present invention may be more fully understood, examples will now be described by way of illustration only with reference to the accompanying drawings, of which:

Figure 1:
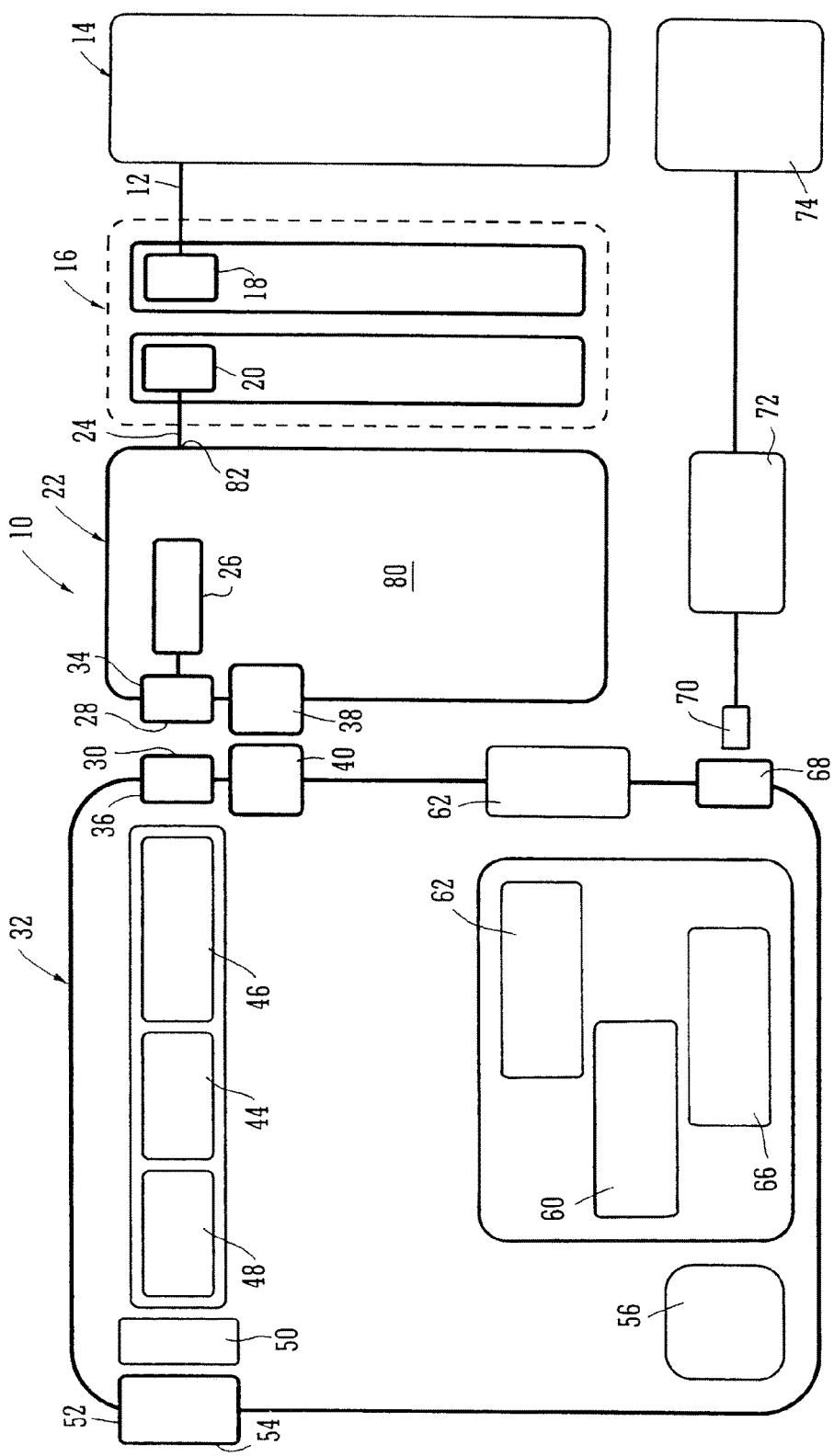
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 μm hydrophobic liquid filter and a 0.2 μm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
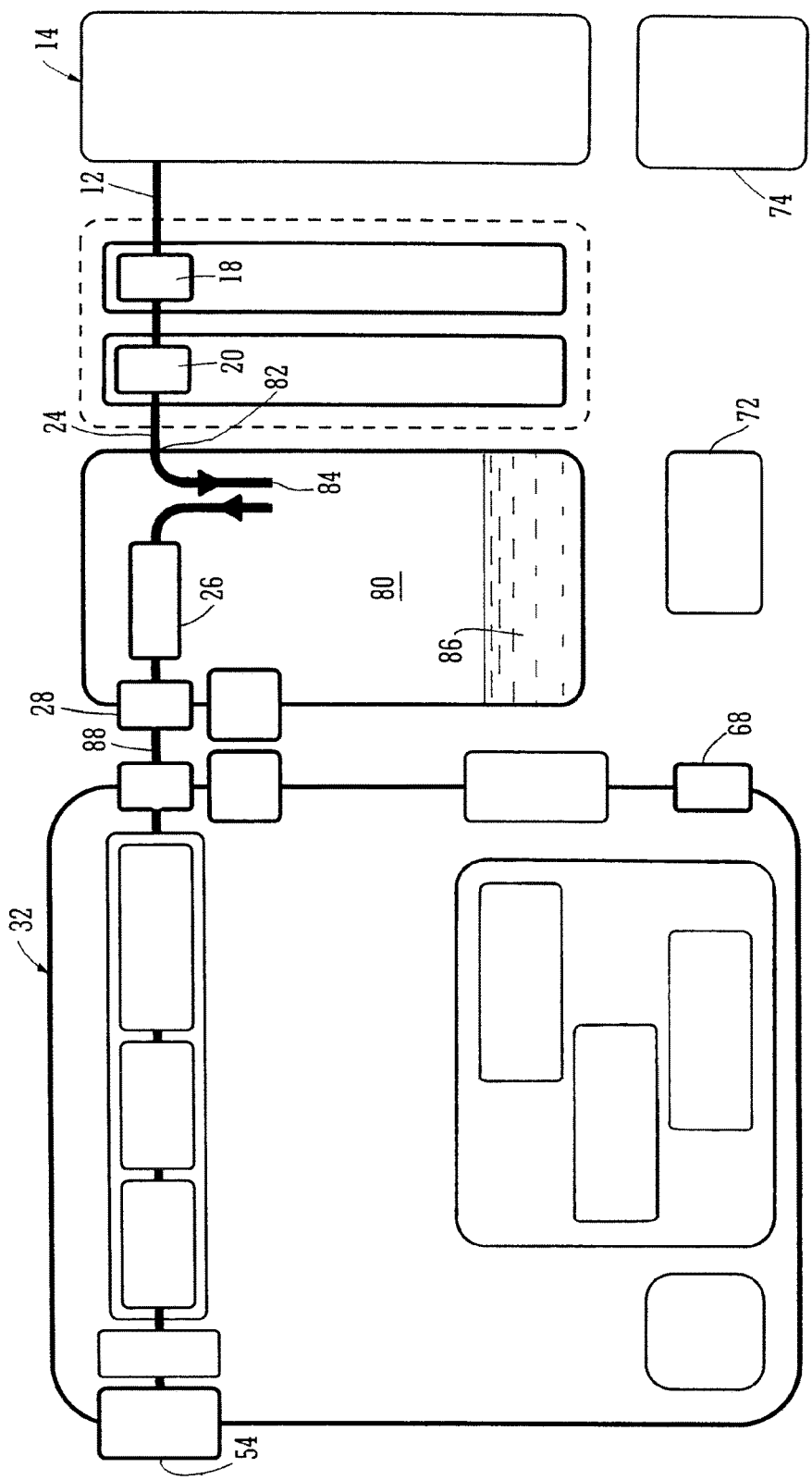
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
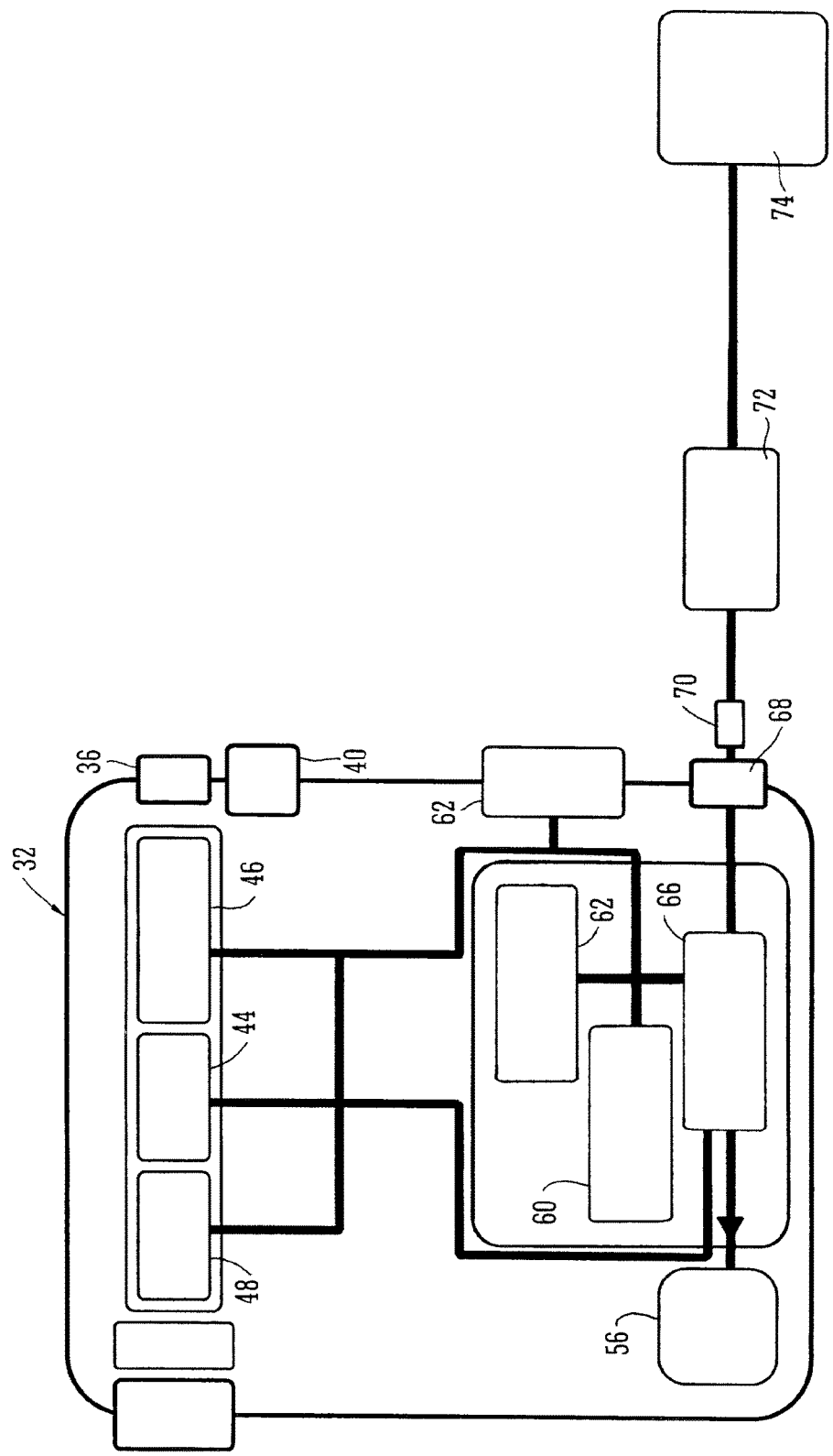
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
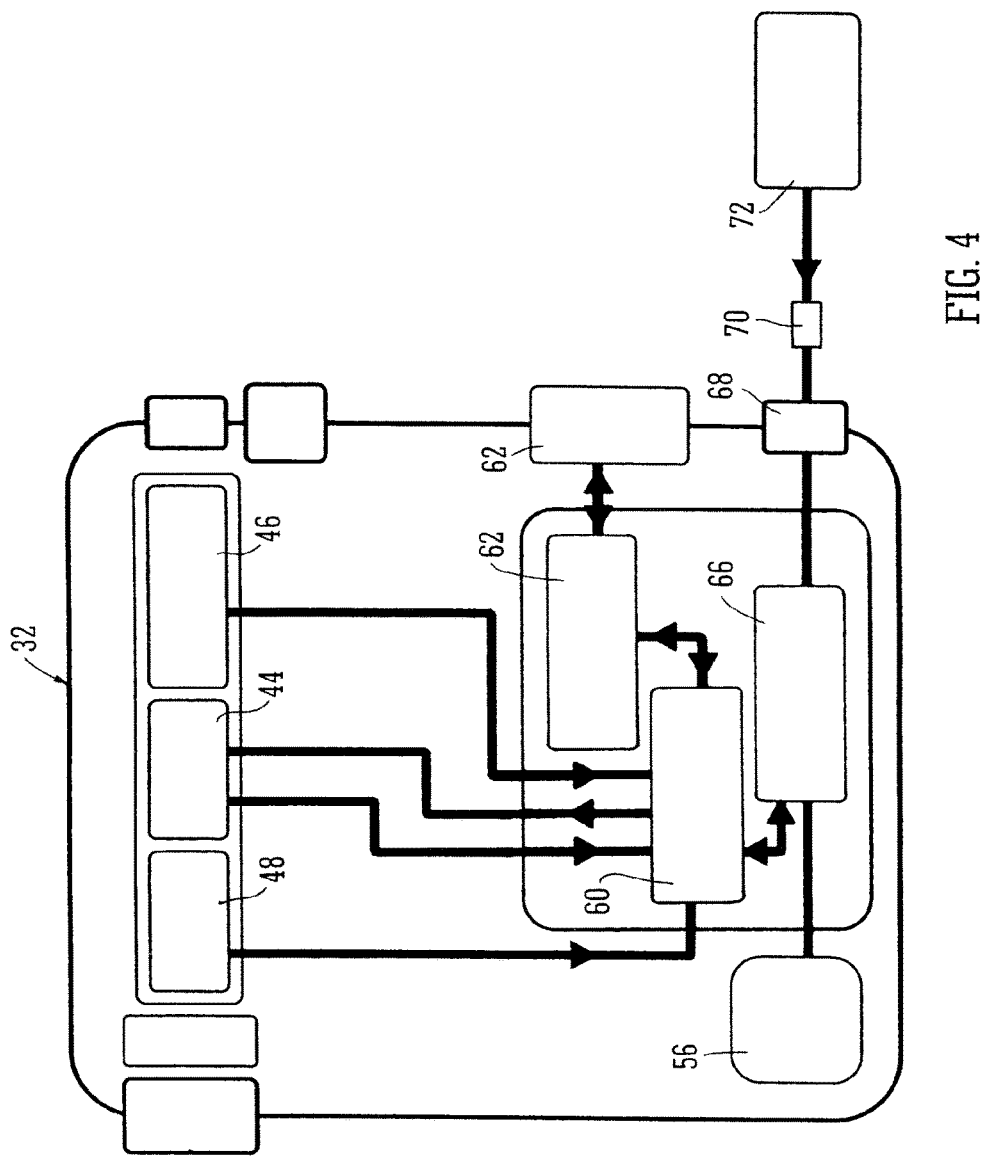
FIG. 4 shows a similar generalised schematic block diagram to FIG. 3 of the device unit and showing control system data paths for controlling the various functions and components of the apparatus.
Figure 5:
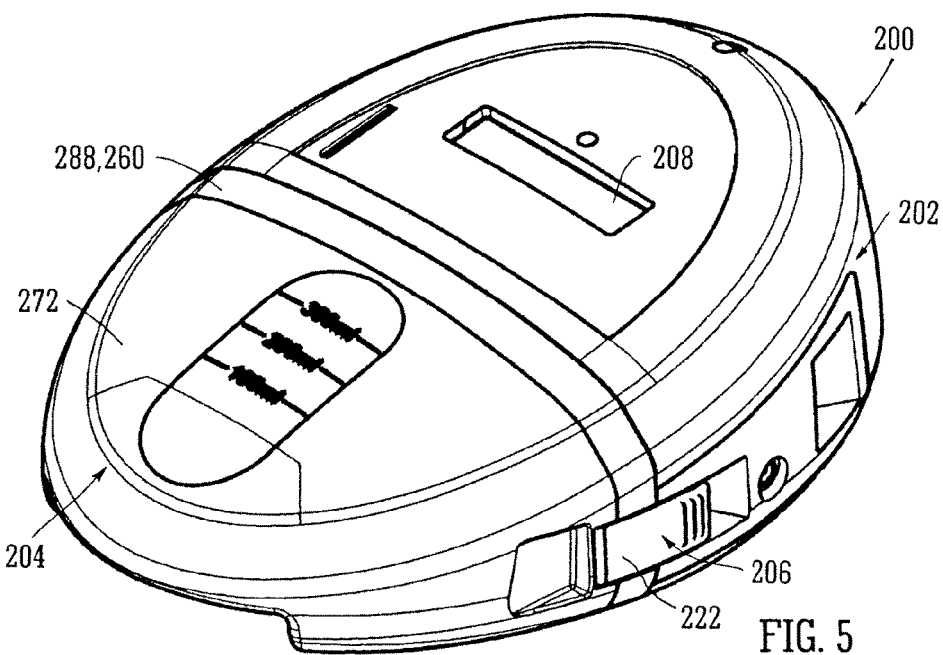
FIG. 5 shows a perspective view of an apparatus.
Figure 6:
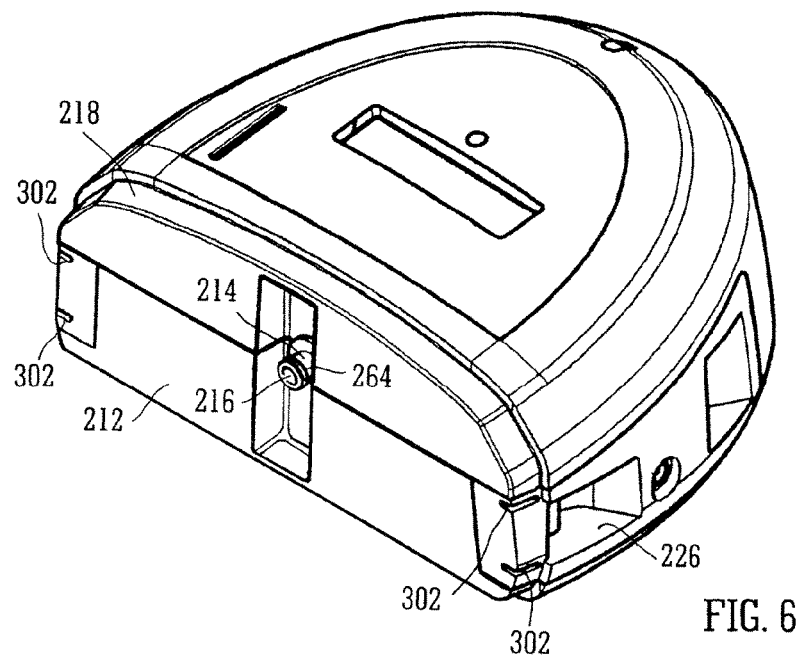
FIG. 6 shows a perspective view of an assembled device unit of the apparatus of FIG. 5.
Figure 7:
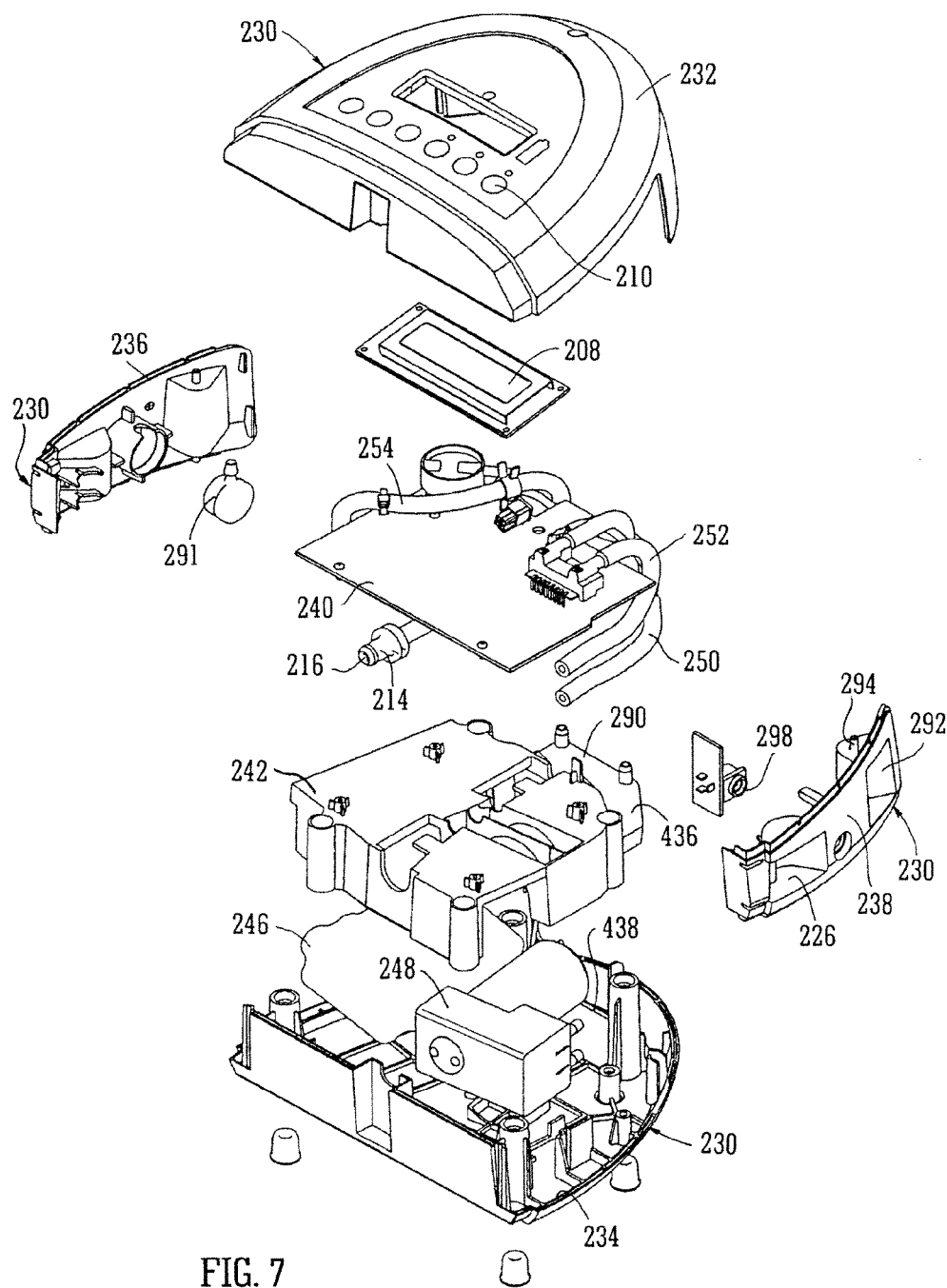
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
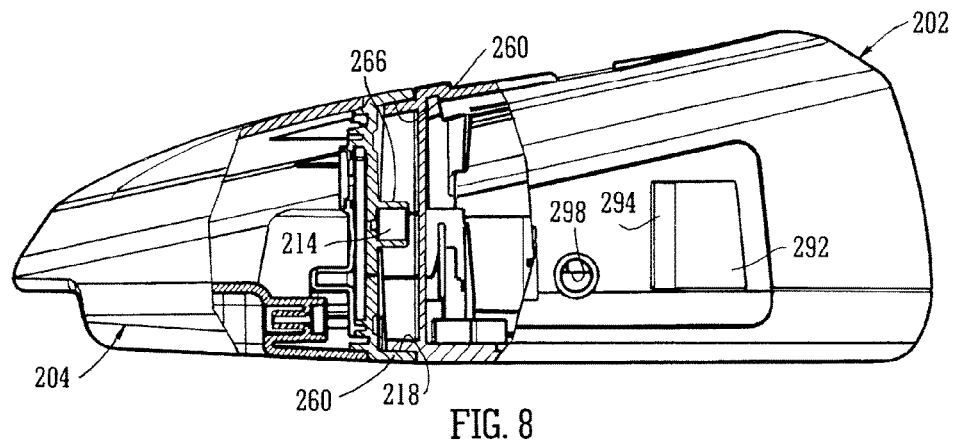
FIG. 8 shows a partially sectioned side elevation view through the interface between a waste canister and device unit of the apparatus.
Figure 9:
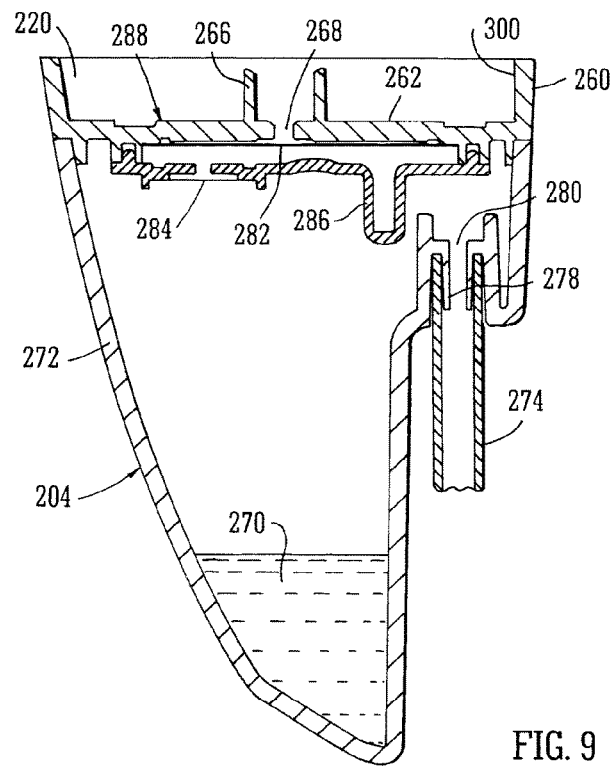
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "0" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 μm filter and 284 comprising a 1 μm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 10:
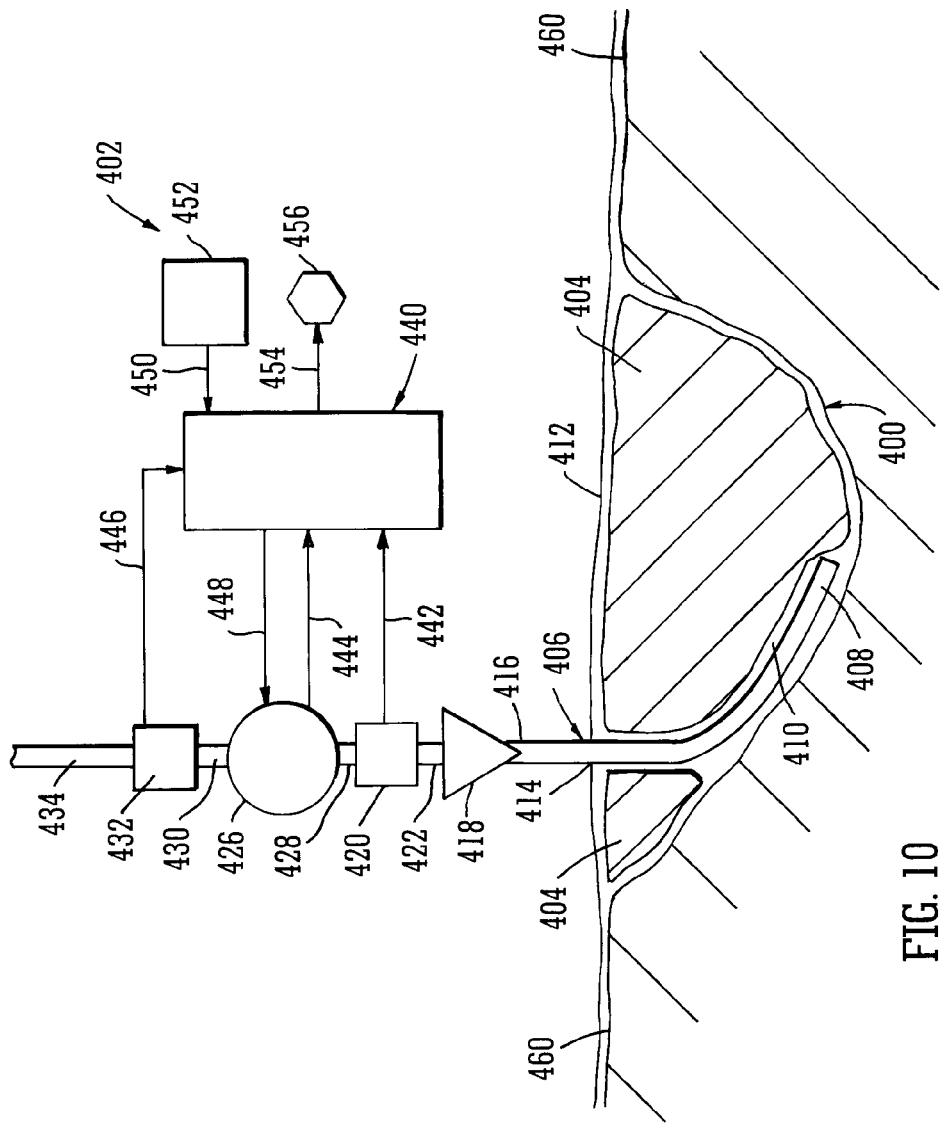
FIG. 10 shows a schematic cross section of a wound, the volume of which is to be measured, the wound having apparatus for the application of TNP therapy thereto.

FIG. 10 shows a schematic cross section of a wound 400 and apparatus 402 connected thereto to apply TNP therapy to the wound and to measure its volume. The apparatus comprises wound filling material 404; an aspirant conduit 406 having one end 408 sealed within the wound cavity 410 by an overlying sealing drape 412 at point 414 and a distal end 416 of the conduit 406 attached to a waste canister 418 for the collection of exudate from the wound. The waste canister is operably connected to a pressure sensor 420 by a conduit portion 422 and to the inlet side of a vacuum pump 426 by a conduit portion 428. The vacuum pump output side is connected by a conduit portion 430 to a flow sensor 432 and exhaust is taken away via a conduit 434. A control and monitoring system is provided at 440 and receives signals 442 from the pressure sensor 420; receives signals 444 from the vacuum pump; and, receives signals 446 from the flow sensor 432. The control system 440 sends control signals 448 to the vacuum pump 426 in order for it to maintain a steady state pressure as set by instructions 450 entered by a clinician/user on a data entry keypad 452. The control system 440 outputs data 454 to a display 456 such as an LCD display, for example, as required by the clinician/user in response to instructions 450 but includes data relating to the volume of the wound 400. The sealing drape 412 is sealed to the patient's sound flesh at 460 surrounding the wound 400 generally by a layer of pressure sensitive adhesive (not shown) on the flesh contacting side of the drape 412.

In operation a clinician/user enters a required pressure, consistent with calibration procedures previously employed, to be achieved in the wound cavity 410 on the keypad 452. The vacuum pump 426 is initiated and pumps the wound cavity 410 down to the required pressure and continues to operate as appropriate to maintain the required pressure at a steady state. The apparatus 402 has been calibrated in that the volumes of the conduit 406; empty waste canister 418; conduits 422, 428, 430; and vacuum pump 426 are known and a correction factor has been entered in the memory of the control system 440.

Figure 11:
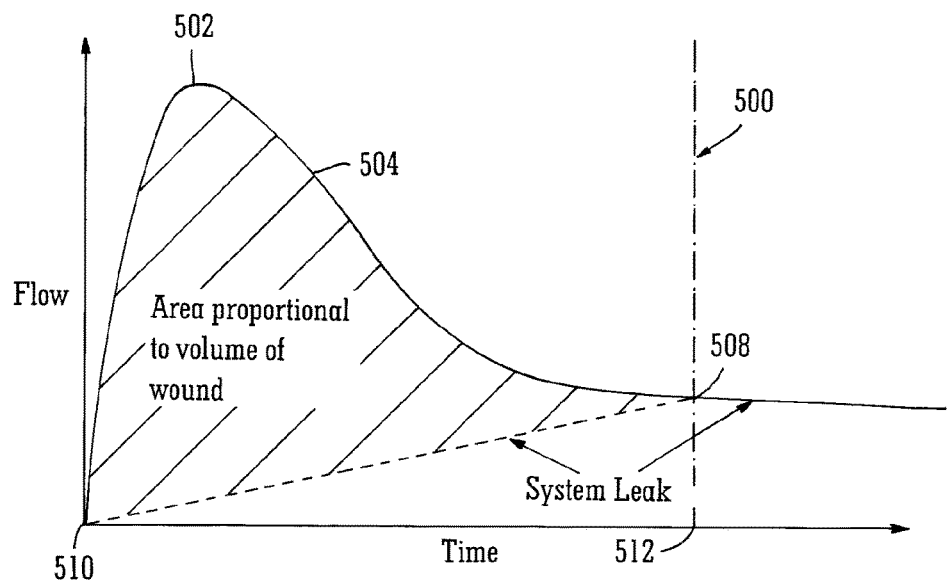
FIG. 11 shows a graph of flow vs time of an example of wound volume measurement.

FIG. 11 shows a graph of fluid flow, in this case air against time to achieve steady state conditions. FIG. 11 indicates time taken to reach a steady state pressure as set in the control system at start up and which time to reach a steady state pressure is indicated by the line 500. Initially the rate of air flow rises rapidly to a maximum at 502 after which the flow rate falls off as the set pressure is approached and the steady state is achieved at line 502. Part of the flow rate under the curve 504 may probably be due to an inward leak of air, most probably into the wound cavity 410 (the joints between the component parts of the apparatus from the conduit 406 in the direction of fluid flow should all be sound and leak-free) between the sealing drape 412 and the patient's sound flesh 460. The point 508 indicates the steady state flow rate to maintain the desired set pressure and the area of the triangle 510, 508, 512 indicates the portion or volume of air aspirated from the wound cavity attributable to the leak and may be deducted from the total area under the curve 504 up to the line 500. Thus, the control and monitoring system 440 computes the volume of the wound from the area under the curve 504 bounded by the line 508-510 and will be displayed on the display 456 and/or in suitable recording apparatus (not shown).

Figure 12:
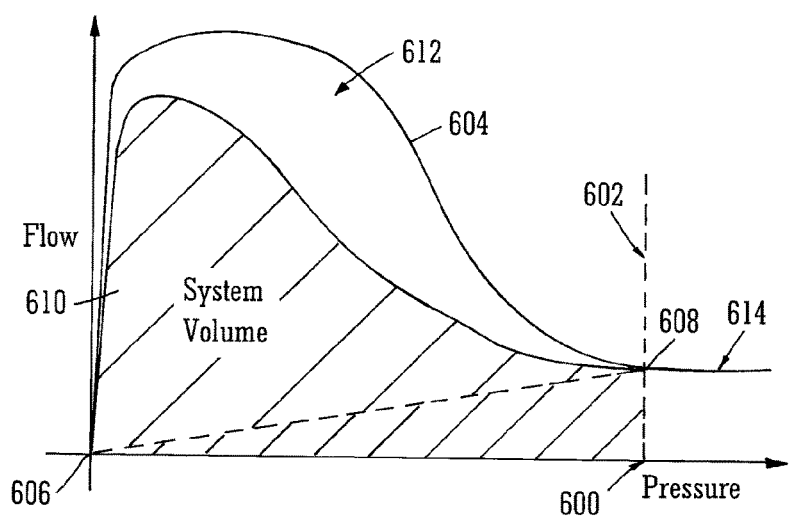
FIG. 12 which shows. a graph of flow against pressure in the wound cavity.

A similar graph to that of FIG. 11 and shown in FIG. 12 may be drawn but showing flow against pressure in the wound cavity 410. Steady state is reached when the set pressure has been achieved. In the graph of FIG. 12 the set pressure 600 and steady state coincide at the line 602 and the total area under the curve 604 is comprised of: a factor relating to leak rate as before and is the triangular area 600, 606, 608; a factor relating to system volume indicated by the vertically hatched area 610 and the wound volume indicated by the area 612. When the system is at a steady state indicated by the line 614 the flow through the flow sensor relates only to the leakage into the system.

The volume of the wound may be computed from the expression:

$$V_{wound} = \text{Area under curve} \times \frac{(760 - \text{Set pressure in mmHg})}{760}$$

If the dressing drape 412 is completely leak-free then the steady state flow rate when the set required pressure is reached will be zero and the point 508 will lie on the time axis.

The flow meter 432 is shown as situated after the vacuum pump 426 but may in other embodiments of apparatus according to the present invention lie between the waste canister 418 and the vacuum pump 426. Suitable correction factors relating to the exact arrangement of apparatus used will need to be determined.

The method of the present invention may be carried out by the apparatus described and discussed with reference to FIGS. 1 to 9 above which also constitutes apparatus according to the present invention.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A negative pressure wound therapy apparatus comprising:
   a source of negative pressure configured to provide negative pressure, via a fluid flow path, to a wound dressing placed over a wound; and
   a controller programmed to operate the source of negative pressure, the controller further programmed to:
      measure a leak rate in the fluid flow path based on a duty cycle of the source of negative pressure;
      provide an indication in response to determining that the measured leak rate exceeds a threshold;
      measure a volume of air extracted from at least the wound;
      determine a wound volume based at least in part on the measured volume of air; and
      correct the determined wound volume based at least in part on the measured leak rate in the fluid flow path.

2. The negative wound therapy of claim 1, wherein the controller is further programmed to:
   determine the duty cycle of the source of negative pressure; and
   activate an alarm in response to determining that the duty cycle exceeds the threshold, wherein the threshold is indicative of a leak in the fluid flow path.

3. The apparatus of claim 1, further comprising a pressure sensor configured to measure pressure in the fluid flow path.

4. The apparatus of claim 3, wherein the pressure sensor is configured to be positioned in the fluid flow path between the source of negative pressure and a waste canister.

5. The apparatus of claim 1, further comprising a flow sensor configured to measure the volume of air extracted from at least the wound.

6. The apparatus of claim 5, wherein the flow sensor comprises a flow meter.

7. The negative wound therapy of claim 1, wherein the controller is further programmed to:
   measure a volume of at least one component located in the fluid flow path to produce a correction factor for determining the wound volume.

8. The apparatus of claim 7, wherein the at least one component located in the fluid flow path comprises at least one of a waste canister, one or more conduits, and the source of negative pressure.

9. The apparatus of claim 8, wherein the controller is further programmed to measure the volume of the waste canister when the waste canister is empty.

10. The apparatus of claim 7, wherein the controller is further programmed to subtract the correction factor from the measured volume of air extracted from at least the wound.

11. The apparatus of claim 1, further comprising a display, wherein the controller is further programmed to provide the cause the corrected wound volume to be displayed on the display.

12. The apparatus of claim 1 wherein the wound volume is computed by a controller programmed to execute software operations.

13. The apparatus of claim 1, wherein the controller is programmed to operate the source of negative pressure to generate negative pressure until a steady state level in the fluid flow path is achieved.

14. A negative pressure wound therapy apparatus comprising:
   a source of negative pressure configured to provide negative pressure, via a fluid flow path, to a wound dressing placed over a wound; and
   a controller programmed to operate the source of negative pressure, the controller further programmed to:
      measure a leak rate in the fluid flow path based on a duty cycle of the source of negative pressure;
      provide an indication in response to determining that the measured leak rate exceeds a threshold; and
      determine the wound volume and correct the determined wound volume when the wound dressing is being changed.

15. The apparatus of claim 14, wherein the controller is further programmed to:
   determine the duty cycle of the source of negative pressure; and
   activate an alarm in response to determining that the duty cycle exceeds the threshold, wherein the threshold is indicative of a leak in the fluid flow path.

16. The apparatus of claim 14, wherein the controller is further programmed to:
   measure a volume of at least one component located in the fluid flow path to produce a correction factor for determining the wound volume.

17. The apparatus of claim 16, wherein the at least one component located in the fluid flow path comprises at least one of a waste canister, one or more conduits, and the source of negative pressure.

18. The apparatus of claim 17, wherein the controller is further programmed to measure the volume of the waste canister when the waste canister is empty.

19. The apparatus of claim 16, wherein the controller is further programmed to subtract the correction factor from the measured volume of air extracted from at least the wound.

20. The apparatus of claim 14, wherein the controller is programmed to operate the source of negative pressure to generate negative pressure until a steady state level in the fluid flow path is achieved.

* * * * *